(12) United States Patent
Noda

(10) Patent No.: US 10,923,624 B2
(45) Date of Patent: Feb. 16, 2021

(54) IMAGING APPARATUS AND ENDOSCOPE

(71) Applicant: Seiko Epson Corporation, Tokyo (JP)

(72) Inventor: Takafumi Noda, Matsumoto (JP)

(73) Assignee: Seiko Epson Corporation

( * ) Notice: Subject to any disclaimer, the term of this patent is extended or adjusted under 35 U.S.C. 154(b) by 351 days.

(21) Appl. No.: 15/970,121

(22) Filed: May 3, 2018

(65) Prior Publication Data

US 2018/0337305 A1 Nov. 22, 2018

(30) Foreign Application Priority Data

May 17, 2017 (JP) ................................. 2017-097932

(51) Int. Cl.
| | |
|---|---|
| A61B 1/00 | (2006.01) |
| H01L 33/08 | (2010.01) |
| H01L 33/60 | (2010.01) |
| H01L 25/16 | (2006.01) |
| A61B 1/06 | (2006.01) |
| A61B 1/05 | (2006.01) |
| B82Y 40/00 | (2011.01) |
| H01L 33/10 | (2010.01) |
| B82Y 20/00 | (2011.01) |

(52) U.S. Cl.
CPC .......... H01L 33/08 (2013.01); A61B 1/00009 (2013.01); A61B 1/00096 (2013.01); A61B 1/00117 (2013.01); A61B 1/00163 (2013.01); A61B 1/00188 (2013.01); A61B 1/051 (2013.01); A61B 1/0638 (2013.01); A61B 1/0676 (2013.01); A61B 1/0684 (2013.01); H01L 25/167 (2013.01); H01L 33/60 (2013.01); B82Y 20/00 (2013.01); B82Y 40/00 (2013.01); H01L 33/10 (2013.01)

(58) Field of Classification Search
None
See application file for complete search history.

(56) References Cited

U.S. PATENT DOCUMENTS

| | | | |
|---|---|---|---|
| 6,240,312 B1 * | 5/2001 | Alfano | A61B 1/00016 128/903 |
| 8,989,528 B2 | 3/2015 | Udd | |
| 2003/0171653 A1 * | 9/2003 | Yokoi | A61B 1/041 600/160 |
| 2005/0154294 A1 * | 7/2005 | Uchiyama | A61B 1/0676 600/420 |
| 2005/0187479 A1 * | 8/2005 | Graumann | A61B 1/04 600/476 |
| 2008/0255409 A1 * | 10/2008 | Graumann | A61B 1/041 600/101 |
| 2010/0038655 A1 * | 2/2010 | Chen | H01L 33/32 257/88 |

(Continued)

FOREIGN PATENT DOCUMENTS

| | | |
|---|---|---|
| JP | 61-011036 A | 1/1986 |
| JP | 61-247444 A | 11/1986 |

(Continued)

*Primary Examiner* — Timothy J Neal
(74) *Attorney, Agent, or Firm* — Harness, Dickey & Pierce, P.L.C.

(57) ABSTRACT

An imaging apparatus including a substrate, an imaging device provided on the substrate, and a light emitting device provided on the substrate and having a plurality of nanostructures.

18 Claims, 7 Drawing Sheets

(56) References Cited

U.S. PATENT DOCUMENTS

| | | | | |
|---|---|---|---|---|
| 2010/0268025 A1* | 10/2010 | Belson | .................. | A61B 1/041 |
| | | | | 600/109 |
| 2013/0243026 A1* | 9/2013 | Noda | ..................... | H01S 5/105 |
| | | | | 372/50.12 |
| 2014/0225139 A1* | 8/2014 | Park | ..................... | H01L 33/483 |
| | | | | 257/98 |
| 2015/0287192 A1* | 10/2015 | Sasaki | .................. | A61B 5/1077 |
| | | | | 382/128 |
| 2016/0131327 A1* | 5/2016 | Moon | ..................... | H01L 33/58 |
| | | | | 362/235 |
| 2016/0338757 A1* | 11/2016 | Luttrull | .................. | A61N 5/025 |
| 2017/0123200 A1* | 5/2017 | Suyama | .................. | A61B 1/041 |

FOREIGN PATENT DOCUMENTS

| | | |
|---|---|---|
| JP | 63-288172 A | 11/1988 |
| JP | 04-134303 A | 5/1992 |
| JP | 06-205789 A | 7/1994 |

\* cited by examiner

IMAGING APPARATUS AND ENDOSCOPE

BACKGROUND

1. Technical Field

The present invention relates to an imaging apparatus and an endoscope.

2. Related Art

There is a known endoscope capable of treatment, such as incision and hemostasis of an organ or any other site, by irradiating a diseased site with laser light.

For example, JP-A-61-11036 describes an endoscope including a semiconductor laser device for treatment based on laser light irradiation and a solid-state imaging device formed of a CCD for observation of the interior of the body of a subject.

The semiconductor laser device (light emitting device) described above, however, generates a large amount of heat and therefore needs a large cooling mechanism in some cases, which prevents size reduction in some cases. Further, since the heat generated by the light emitting device affects the imaging device in some cases, the light emitting device and the imaging device cannot be so arranged as to be close to each other and therefore does not allow size reduction in some cases.

SUMMARY

An advantage of some aspects of the invention is to provide an imaging apparatus that includes a light emitting device and an imaging device and allows size reduction. Another advantage of some aspects of the invention is to provide an endoscope including the imaging apparatus.

An imaging apparatus according to an aspect of the invention includes a substrate, an imaging device provided on the substrate, and a light emitting device provided on the substrate and having a plurality of nano-structures.

In the thus configured imaging apparatus, the light emitting device having a plurality of nano-structures generates only a small amount of heat and therefore does not need a large cooling mechanism. Further, in the imaging apparatus, the light emitting device and the imaging device can be so arranged as to be close to each other. Moreover, in the imaging apparatus, the imaging device and the light emitting device are provided on the same substrate. The size of the imaging apparatus can therefore be reduced.

In the imaging apparatus according to the aspect of the invention, the substrate may have a nano-structure formation area in which the nano-structures are provided, and the nano-structure formation area may be so provided as to surround the imaging device in a plan view.

In the thus configured imaging apparatus, light emitted from the light emitting device and reflected off a target to be imaged can be more reliably received.

In the imaging apparatus according to the aspect of the invention, the substrate may have a first nano-structure formation area and a second nano-structure formation area in each of which the nano-structures are provided, and a wavelength of light outputted from the nano-structures provided in the first nano-structure formation area may differ from a wavelength of light outputted from the nano-structures provided in the second nano-structure formation area.

In a case where the thus configured imaging apparatus is used as an endoscope, the wavelength of the light outputted from the imaging apparatus can be selected (switched) in accordance with the type of a diseased site or the application in which the imaging apparatus is used.

In the imaging apparatus according to the aspect of the invention, the substrate may have a third nano-structure formation area in which the nano-structures are provided, the light outputted from the nano-structures provided in the first nano-structure formation area may be red light, the light outputted from the nano-structures provided in the second nano-structure formation area may be green light, and light outputted from the nano-structures provided in the third nano-structure formation area may be blue light.

The thus configured imaging apparatus can output light beams having a larger number of wavelengths, for example, can output white light.

The imaging apparatus according to the aspect of the invention may further include a collector lens and a diffuser lens, in which the substrate may have a laser light outputting area and a LED light outputting area in each of which the nano-structures are provided, light outputted from the nano-structures provided in the laser light outputting area may be laser light and may be incident on the collector lens, and light outputted from the nano-structures provided in the LED light outputting area may be LED light and may be incident on the diffuser lens.

In the thus configured imaging apparatus, the collector lens can output the laser light incident thereon at a narrower angle of radiation, whereby in a case where the imaging apparatus is used as an endoscope, incision and excision can be readily performed on a diseased site. Further, in the imaging apparatus, the diffuser lens can output the LED light incident thereon at a wider angle of radiation, whereby in the case where the imaging apparatus is used as an endoscope, a diseased site can be observed over a wider range.

In the imaging apparatus according to the aspect of the invention, the imaging device and the light emitting device may be provided on first surface of the substrate.

In the thus configured imaging apparatus, the light emitting device can be readily positioned with respect to the imaging device.

In the imaging apparatus according to the aspect of the invention, the light emitting device may be provided on a first surface of the substrate, and the imaging device may be provided on a second surface of the substrate that faces away from the first surface.

In the thus configured imaging apparatus, for example, the light emitting device can be readily formed.

An endoscope according to another aspect of the invention includes the imaging apparatus according to the aspect of the invention.

In the thus configured endoscope, which includes the imaging apparatus according to the aspect of the invention, the size of a portion inserted into the body of a subject can be reduced.

BRIEF DESCRIPTION OF THE DRAWINGS

The invention will be described with reference to the accompanying drawings, wherein like numbers reference like elements.

DESCRIPTION OF EXEMPLARY EMBODIMENTS

Preferable embodiments of the invention will be described below in detail with reference to the drawings. It is not intended that the embodiments described below unduly limit the contents of the invention set forth in the appended claims. Further, all configurations described below are not necessarily essential configuration requirements of the invention.

1. First Embodiment

1.1. Imaging Apparatus

Figure 1:
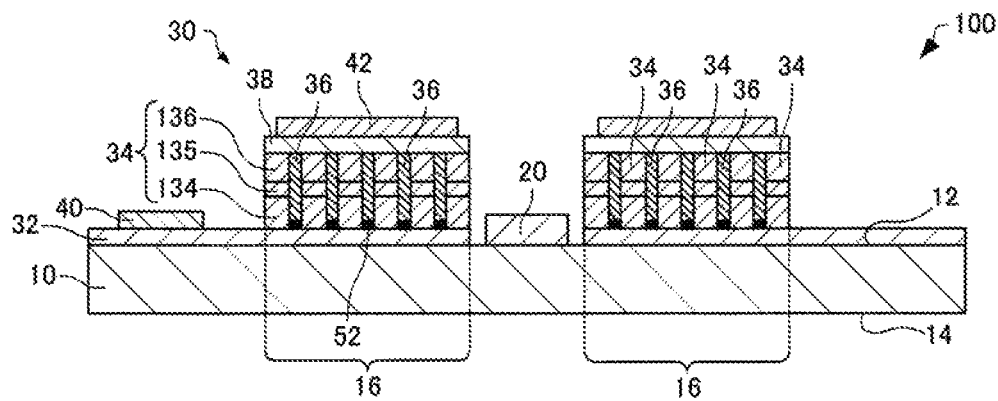
FIG. 1 is a cross-sectional view diagrammatically showing an imaging apparatus according to a first embodiment.
Figure 2:
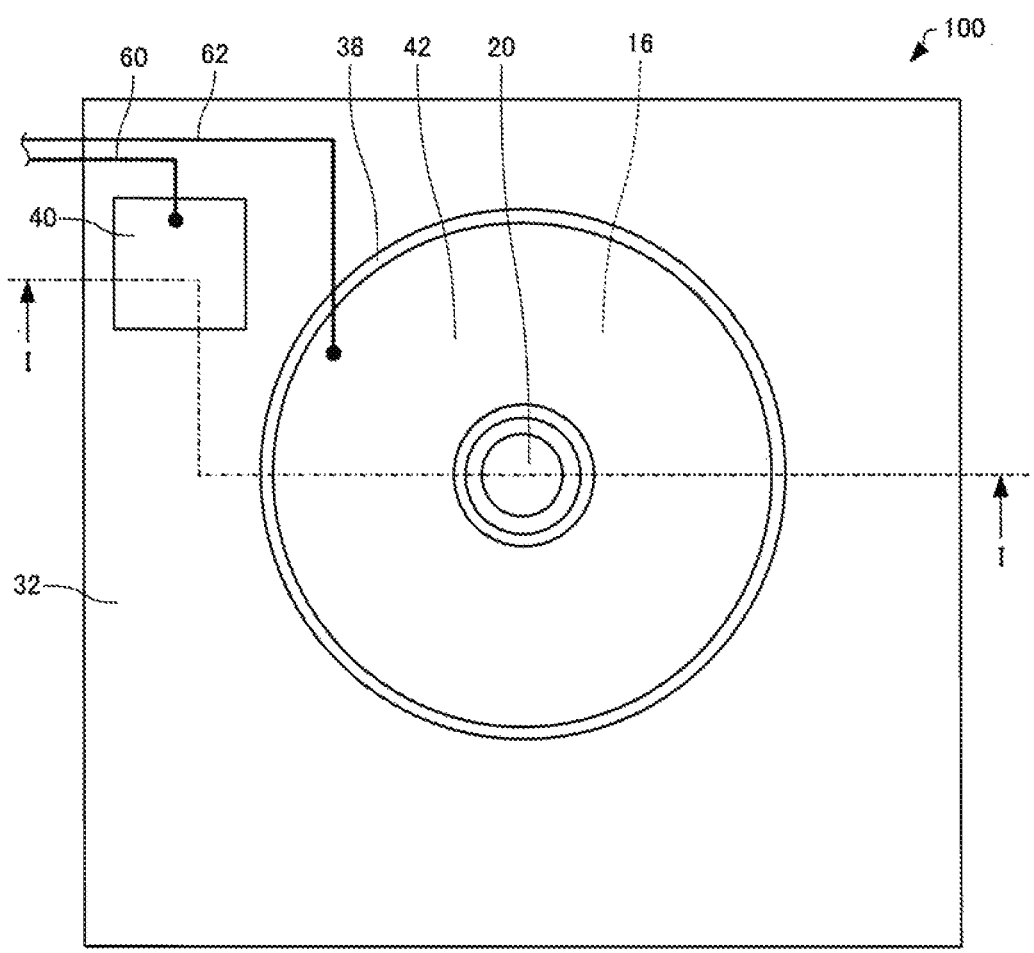
FIG. 2 is a plan view diagrammatically showing the imaging apparatus according to the first embodiment.

An imaging apparatus according to a first embodiment will first be described with reference to the drawings. FIG. 1 is a cross-sectional view diagrammatically showing an imaging apparatus 100 according to the present embodiment. FIG. 2 is a plan view diagrammatically showing the imaging apparatus 100 according to the first embodiment. FIG. 1 is the cross-sectional view taken along the line I-I in FIG. 2.

An imaging apparatus 100 includes a substrate 10, an imaging device 20, and a light emitting device 30, as shown in FIGS. 1 and 2.

The substrate 10 has a plate-like shape. The substrate 10 has a first surface 12 and a second surface 14, which faces away from the first surface 12. The substrate 10 is a semiconductor substrate, for example, a Si substrate or a GaN substrate. The substrate 10 may include an insulating substrate, such as a sapphire substrate, and a semiconductor substrate provided on the insulating substrate.

The imaging device 20 is provided on the substrate 10. The imaging device 20 is provided on the first surface 12 of the substrate 10. The imaging device 20 can receive light from a target to be imaged to produce electric charge and transfer the electric charge to an external apparatus. The imaging device 20 is, for example, a CCD image sensor including a plurality of photodiodes that each produce electric charge in accordance with the intensity of the light incident thereon and a CCD (charge-coupled device) that transfers the electric charge produced by the photodiodes to an external apparatus. The imaging device 20 can receive light emitted from the light emitting device 30 and reflected off the target to be imaged. The imaging device 20 does not necessarily have a specific plan shape and has a circular shape in the example shown in FIG. 2.

The imaging device 20 may instead be a CMOS (complementary metal oxide semiconductor) image sensor so formed that each of the photodiodes is paired with one amplifier.

The light emitting device 30 is provided on the substrate 10. The light emitting device 30 is provided on the first surface 12 of the substrate 10. The imaging device 20 and the light emitting device 30 are provided on the same substrate 10. The light emitting device 30 can irradiate an area an image of which the imaging device 20 captures.

The light emitting device 30 includes, for example, a first contact layer 32, nano-structures 34, light propagating members 36, a second contact layer 38, a first electrode 40, and a second electrode 42.

The first contact layer 32 is provided on the substrate 10. The first contact layer 32 is a layer that is in ohmic-contact with the first electrode 40. The first contact layer 32 is, for example, a first-conductivity-type (n-type, for example) GaN layer.

The nano-structures 34 are provided on the first contact layer 32. The substrate 10 has a nano-structure formation area 16, where the nano-structures 34 are provided via the first contact layer 32. The nano-structure formation area 16 is configured by the first surface 12 of the substrate 10. The nano-structure formation area 16 is so provided as to surround the imaging device 20 in a plan view. The nano-structure formation area 16 is the area where the first contact layer 32 and the second contact layer 38 overlap with each other in the plan view. In the example shown in FIG. 2, the nano-structure formation area 16 has the same plan shape as that of the second contact layer 38, which is an annular shape.

The nano-structures 34 are provided in plurality. The nano-structures 34 are each, for example, a nano-scale columnar structure extending upward from the upper surface of the first contact layer 32. Such a nano-scale columnar structure is also called, for example, a nano-wire and a nano-rod.

The nano-structures 34 each have, for example, a circular columnar shape. The diameter of each of the nano-structures 34 is a diameter of the order of nanometers and is, for example, greater than or equal to 50 nm but smaller than or equal to 500 nm. The height of each of the nano-structures 34 is, for example, greater than or equal to 0.1 µm but smaller than or equal to 5 µm. The plurality of nano-structures 34 are separate from each other. The distance between adjacent nano-structures 34 is, for example, greater than or equal to 1 nm but smaller than or equal to 500 nm.

The plurality of nano-structures 34 are provided, for example, in a matrix in the plan view. For example, let λ be the wavelength of light produced in the nano-structures 34 and n be the average refractive index of the nano-structures 34 including light emitting layers 135 (average refractive index in direction perpendicular to thickness direction of light emitting layers 135 (upward/downward direction)), and arranging the nano-structures 34 at intervals λ/(2n) allows the light emitting device 30 to emit polarized light.

The nano-structures 34 each have a first semiconductor layer 134, the light emitting layer, and a second semiconductor layer 136.

The first semiconductor layer 134 is provided on the first contact layer 32. The first semiconductor layer 134 is, for example, a first-conductivity-type (n-type, for example) GaN layer.

The light emitting layer 135 is provided on the first semiconductor layer 134. The light emitting layer 135 is a layer capable of emitting light when current is injected thereinto. The light emitting layer 135 has a quantum well structure formed, for example, of a GaN layer and an InGaN layer.

The second semiconductor layer 136 is provided on the light emitting layer 135. The second semiconductor layer 136 is, for example, a second-conductivity-type (p-type, for example) GaN layer. The semiconductor layers 134 and 136 are each a cladding layer having the function of confining light in an active layer 34 (preventing light from leaking from active layer 34).

The light propagating members 36 are each provided between adjacent nano-structures 34. The light propagating members 36 are each, for example, a GaN layer (GaN layer into which Si is doped, for example). The light propagating members 36 allow light produced in the light emitting layers 135 to propagate. In the example shown in FIG. 1, a mask layer 52, which serves as a mask when the nano-structures 34 are formed, is provided between the light propagating members 36 and the first contact layer 32.

In the light emitting device 30, the p-type second semiconductor layer 136, the light emitting layer 135, into which no impurity is doped, and the n-type first semiconductor layer 134 form a pin diode in each of the nano-structures 34. The first semiconductor layer 134 and the second semiconductor layer 136 are each a layer having a bandgap wider than that of the light emitting layer 135. In the light emitting device 30, when forward bias voltage for the pin diode is applied to (current is injected into) the portion between the first electrode 40 and the second electrode 42, electrons and holes recombine with each other in each of the light emitting layers 135. The recombination leads to light emission. The light emitting device 30 can therefore emit light from above (second electrode 42 side) and from a downward direction (substrate 10 side).

Although not shown, a reflection layer may be provided between the substrate 10 and the first contact layer 32. The reflection layer is, for example, a DBR (distributed Bragg reflector) layer. The reflection layer can reflect the light produced in the light emitting layers 135, and the light emitting device 30 can therefore emit light only through the second electrode 42.

The light emitting device 30 can function as an LED (light emitting diode) device and emit LED light and can function as a laser device and emit laser light depending on the amount of current injected into the light emitting layers 135. Specifically, when the current injected into the light emitting layers 135 is lower than threshold current (minimum current that allows laser oscillation), the light emitting device 30 emits the LED light, whereas when the current injected into the light emitting layers 135 is higher than or equal to the threshold current, the light emitting device 30 emits the laser light.

The plurality of nano-structures 34 are so arranged that when current lower than the threshold current is injected into the light emitting layers 135, light spontaneously emitted in the light emitting layers 135 propagates laterally (direction perpendicular to thickness direction of light emitting layers 135 (upward/downward direction)) and the propagating light resonates, whereas when current higher than or equal to the threshold current is injected into the light emitting layers 135, the light emitting device 30 transitions to a stimulated light emission state and can emit +first-order diffracted light and −first-order diffracted light in the form of laser light upward and downward.

The second contact layer 38 is provided on the nano-structures 34. Specifically, the second contact layer 38 is provided on the second semiconductor layers 136 and the light propagating members 36. In the example shown in FIG. 2, the second contact layer 38 has an annular plan shape. The second contact layer 38 is a layer that is in ohmic-contact with the second electrode 42. The second contact layer 38 is, for example, a second-conductivity-type (p-type, for example) GaN layer.

The first electrode 40 is provided on the first contact layer 32. In the example shown in FIG. 2, the first electrode 40 has a rectangular plan shape. The first electrode 40 is electrically connected to the first semiconductor layers 134 via the first contact layer 32. The first electrode 40 is one electrode for injecting the current into the light emitting layers 135. The first electrode 40 is, for example, an electrode formed of a Ti layer, an Al layer, and an Au layer layered in this order from the side facing the first contact layer 32.

The second electrode 42 is provided on the second contact layer 38. In the example shown in FIG. 2, the second electrode 42 has an annular plan shape. The second electrode 42 is electrically connected to the second semiconductor layers 136 via the second contact layer 38. The second electrode 42 is the other electrode for injecting the current into the light emitting layers 135. The second electrode 42 is a transparent electrode made, for example, of ITO (indium tin oxide). The light emitted from the light emitting layers 135 can therefore pass through and out of the second electrode 42.

The electrodes 40 and 42 of the light emitting device 30 are connected to wiring lines 60 and 62, respectively. The wiring lines 60 and 62 are connected to a drive circuit that is not shown. The output from the light emitting device 30 has, for example, a magnitude of several watts.

The imaging apparatus 100 has, for example, the following features.

The imaging apparatus 100 includes the light emitting device 30 including the plurality of nano-structures 34. The light emitting device 30 including the plurality of nano-structures 34 has high quantum efficiency and therefore generates a small amount of heat as compared with an edge emitting semiconductor laser, which emits light in the direction perpendicular to the thickness direction of the light emitting layers 135, and a vertical cavity surface emitting laser (VCSEL) and therefore does not need a large cooling mechanism. Therefore, in the imaging apparatus 100, the size of the light emitting device 30 can be reduced. Further, in the imaging apparatus 100, in which the light emitting device 30 generates only a small amount of heat, heat generated by the light emitting device 30 affects the imaging device 20 only by a small degree. Therefore in the imaging apparatus 100, the light emitting device 30 and the imaging device 20 can be so arranged as to be close to each other for reduction of the size of the imaging apparatus 100.

Further, in the imaging apparatus 100, the imaging device 20 and the light emitting device 30 are provided on the same substrate 10. Therefore, in the imaging apparatus 100, the number of parts, for example, can be reduced as compared with a case where the imaging device 20 and the light emitting device 30 are provided on separate substrates, whereby the size of the imaging apparatus 100 can be reduced.

As described above, the size of the imaging apparatus 100 can be reduced.

In the imaging apparatus 100, the nano-structure formation area 16 is so provided as to surround the imaging device 20 in the plan view. Therefore, in the imaging apparatus 100, the light emitted from the light emitting device 30 and reflected off a target to be imaged can be more reliably received. For example, in the case of a VCSEL, two mirror layers need to be so arranged in the upward/downward direction as to sandwich a light emitting layer to form a resonator, and it is therefore difficult in some cases to achieve an arrangement in which the VCSEL surrounds the imaging device 20.

In the imaging apparatus 100, the imaging device 20 and the light emitting device 30 are provided on the first surface 12 of the substrate 10. Therefore, in the imaging apparatus 100, the light emitting device 30 can be readily positioned with respect to the imaging device 20 as compared with a case where the imaging device 20 and the light emitting device 30 are provided on separate surfaces.

1.2. Method for Manufacturing Imaging Apparatus

A method for manufacturing the imaging apparatus 100 according to the first embodiment will next be described with reference to the drawings. FIGS. 3 to 7 are cross-sectional views diagrammatically showing the steps of manufacturing the imaging apparatus 100 according to the first embodiment.

Figure 3:
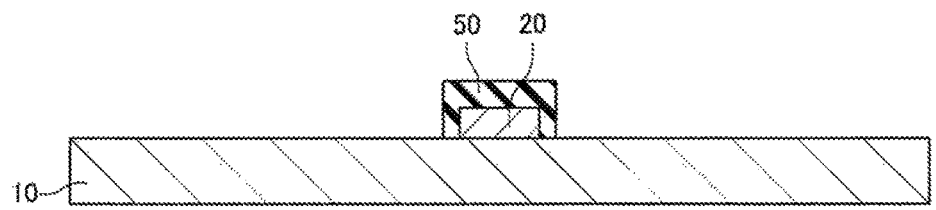
FIG. 3 is a cross-sectional view diagrammatically showing one of the steps of manufacturing the imaging apparatus according to the first embodiment.

The imaging device 20 is formed on the substrate 10, as shown in FIG. 3. Specifically, a semiconductor layer (not shown) or any other layer is formed on the substrate 10, and the semiconductor layer is processed in a semiconductor manufacturing process to form the imaging device 20 on the substrate 10. It is noted that the imaging device 20 may be prepared, and the imaging device 20 may be bonded onto the substrate 10 via a bonding member. The imaging device 20 is then covered with a protective layer 50. The protective layer 50 is, for example, a resist layer.

Figure 4:
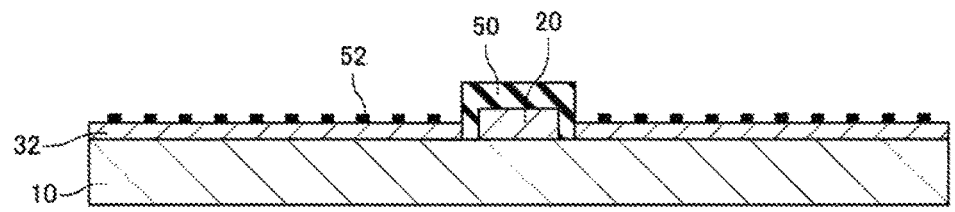
FIG. 4 is a cross-sectional view diagrammatically showing one of the steps of manufacturing the imaging apparatus according to the first embodiment.

The first contact layer 32 is formed on the substrate 10 in an epitaxial growth process, as shown in FIG. 4. A method for allowing the epitaxial growth is, for example, an MOCVD (metal organic chemical vapor deposition) method and an MBE (molecular beam epitaxy) method.

The mask layer 52 is then formed on the first contact layer 32. The mask layer 52 is, for example, a metal layer made, for example, of Ti, an insulating layer formed, for example, of a silicon oxide layer, or a laminate thereof. The mask layer 52 is formed by film deposition using the MOCVD method, the MBE method, or any other method and patterning based on photolithography and etching technologies.

Figure 5:
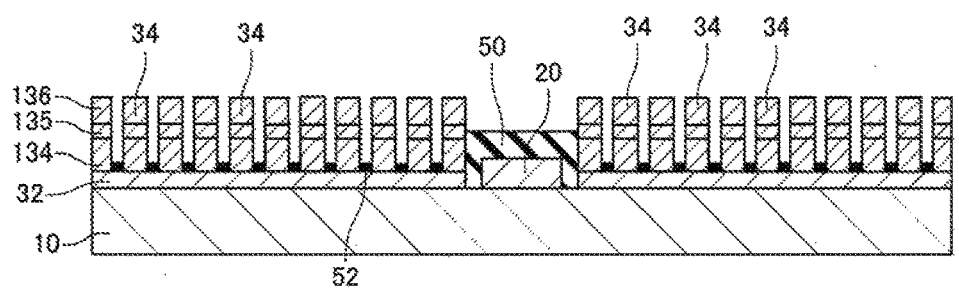
FIG. 5 is a cross-sectional view diagrammatically showing one of the steps of manufacturing the imaging apparatus according to the first embodiment.

The mask layer 52 is used as mask to form the first semiconductor layers 134, the light emitting layers 135, and the second semiconductor layers 136 in this order on the first contact layer 32, as shown in FIG. 5. The present step allows formation of the plurality of nano-structures 34.

Figure 6:
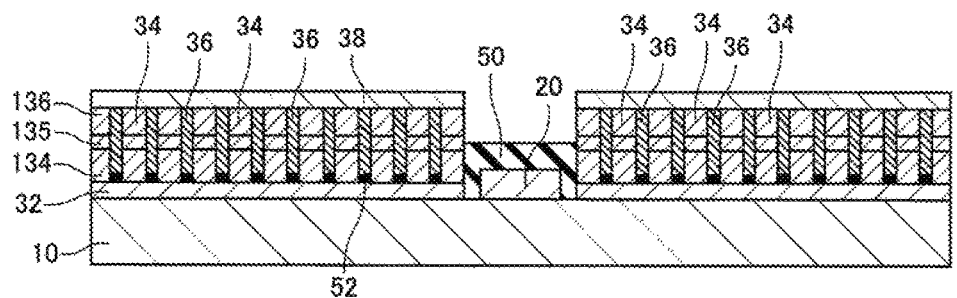
FIG. 6 is a cross-sectional view diagrammatically showing one of the steps of manufacturing the imaging apparatus according to the first embodiment.

The light propagating members 36 are each formed between adjacent nano-structures 34, as shown in FIG. 6. The light propagating members 36 are formed, for example, in an epitaxial lateral overgrowth process using the MOCVD method. After the light propagating members 36 are formed, part of the nano-structures 34 and part of the light propagating members 36 may be so removed, for example, by CMP (chemical mechanical polishing) that the upper surfaces of the nano-structures 34 are flush with the upper surfaces of the light propagating members 36.

The second contact layer 38 is then formed on the nano-structures 34 and the light propagating members 36 in an epitaxial growth process. A method for allowing the epitaxial growth is, for example, the MOCVD and the MBE method.

Figure 7:
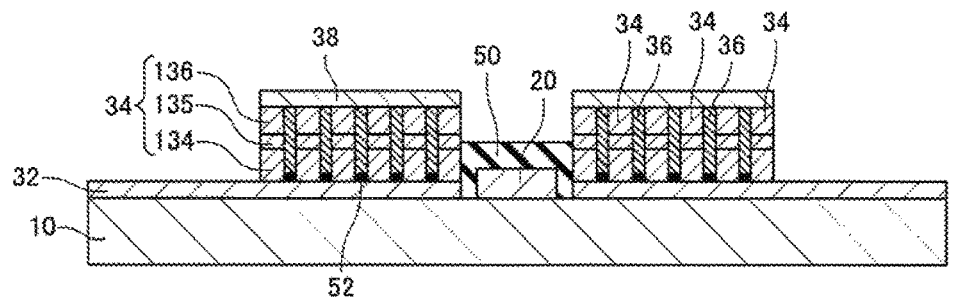
FIG. 7 is a cross-sectional view diagrammatically showing one of the steps of manufacturing the imaging apparatus according to the first embodiment.

A mask layer (not shown) having a predetermined shape is used as a mask to etch the second contact layer 38 and the nano-structures 34 into the predetermined shape, as shown in FIG. 7.

The first electrode 40 is formed on the first contact layer 32, and the second electrode 42 is formed on the second contact layer 38, as shown in FIG. 1. The first electrode 40 and the second electrode 42 are formed, for example, by using a vacuum evaporation method. The steps described above allow formation of the light emitting device 30. The protective layer 50 is then removed.

The steps described above allow the imaging apparatus 100 to be manufactured.

In the example described above, the light emitting device 30 is formed after the imaging device 20 is formed. Instead, the imaging device 20 may be formed after the light emitting device 30 is formed.

1.3. Variations of Imaging Apparatus 1.3.1. First Variation

Figure 8:
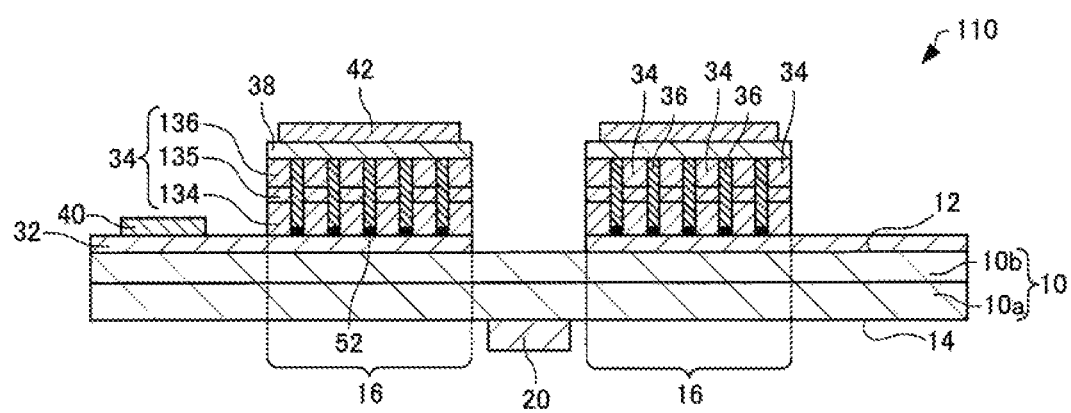
FIG. 8 is a cross-sectional view diagrammatically showing an imaging apparatus according to a first variation of the first embodiment.

An imaging apparatus according to a first variation of the first embodiment will next be described with reference to the drawings. FIG. 8 is a cross-sectional view diagrammatically showing an imaging apparatus 110 according to the first variation of the first embodiment.

In the imaging apparatus 110 according to the first variation of the first embodiment in the following description, members having the same functions as those of the constituent members of the imaging apparatus 100 according to the first embodiment described above have the same reference characters and will not be described in detail. The same holds true for an imaging apparatus according to a second variation of the first embodiment, which will be described later.

In the imaging apparatus 100 described above, the imaging device 20 and the light emitting device 30 are provided on the first surface 12 of the substrate 10, as shown in FIG. 1. In contrast, in the imaging apparatus 110, the light emitting device 30 is provided on the first surface 12 of the substrate 10, and the imaging device 20 is provided on the second surface 14 of the substrate 10, as shown in FIG. 8.

In the imaging apparatus 110, the substrate 10 includes, for example, a first substrate 10a and a second substrate 10b, which is provided on the first substrate 10a. The lower surface of the first substrate 10a is the second surface 14. The first substrate 10a is, for example, a Si substrate, which readily allows the formation of the imaging device 20. The imaging device 20 can receive light having passed through the substrate 10. The upper surface of the second substrate 10b is the first surface 12. The second substrate 10b is, for example, a GaN substrate, which readily allows the formation of the light emitting device 30.

In the imaging apparatus 110, the light emitting device 30 is provided on the first surface 12 of the substrate 10, and the imaging device 20 is provided on the second surface 14 of the substrate 10. Therefore, in the imaging apparatus 110, in which the surface on which the imaging device 20 is provided differs from the surface on which the light emitting device 30 is provided, the protective layer 50, which covers the imaging device 20 as shown in FIG. 3, does not need to be formed, whereby the light emitting device 30 can be readily formed.

1.3.2. Second Variation

Figure 9:
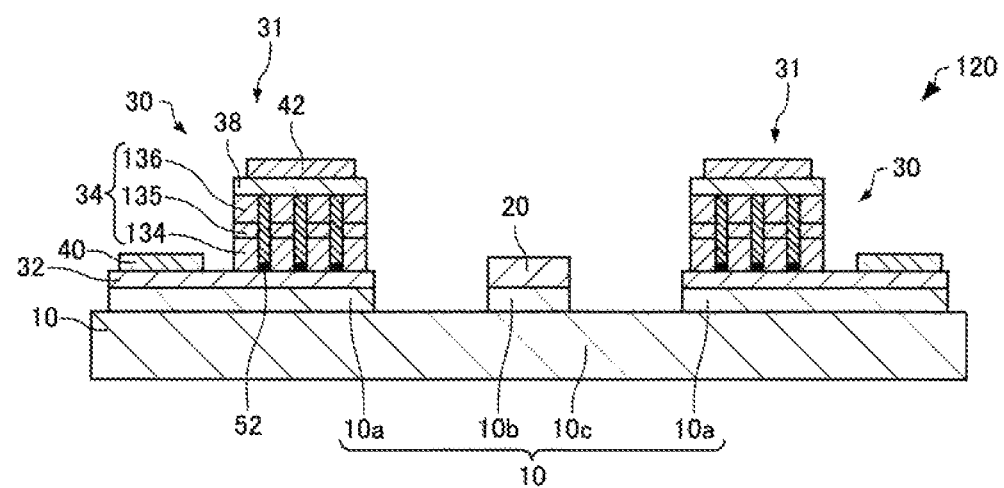
FIG. 9 is a cross-sectional view diagrammatically showing an imaging apparatus according to a second variation of the first embodiment.
Figure 10:
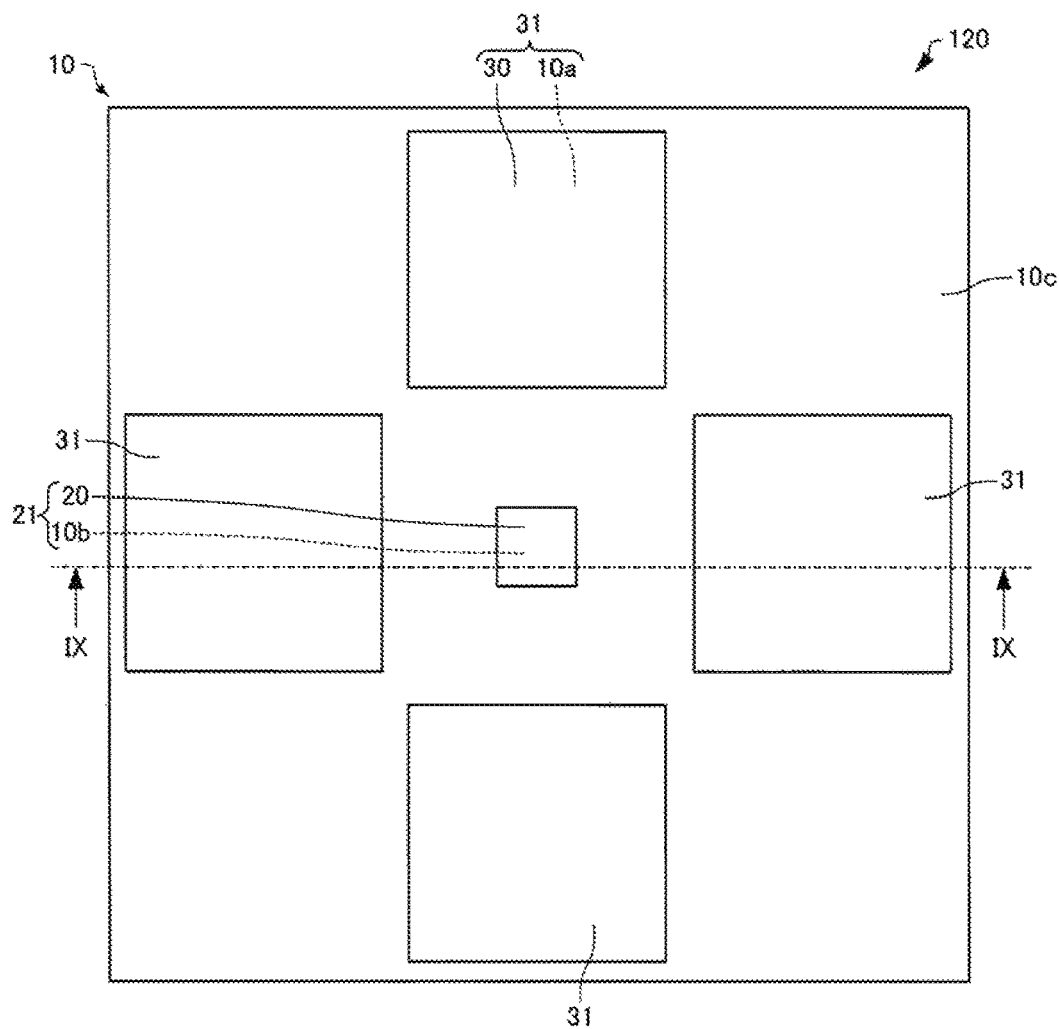
FIG. 10 is a plan view diagrammatically showing the imaging apparatus according to the second variation of the first embodiment.

An imaging apparatus according to a second variation of the first embodiment will next be described with reference to the drawings. FIG. 9 is a cross-sectional view diagrammatically showing an imaging apparatus 120 according to the second variation of the first embodiment. FIG. 10 is a plan view diagrammatically showing the imaging apparatus 120 according to the second variation of the first embodiment. FIG. 9 is the cross-sectional view taken along the line IX-IX shown in FIG. 10.

The imaging apparatus 120 differs from the imaging apparatus 100 described above in that the substrate 10 includes first substrates 10a, a second substrate 10b, and a third substrate 10c, as shown in FIGS. 9 and 10.

The third substrate 10c is, for example, a printed circuit board. The first substrates 10a are provided on the third substrate 10c. In the example shown in FIGS. 9 and 10, the first substrates 10a are formed of four substrates 10a, but the number of first substrates 10a is not limited to a specific number. The first substrates 10a are each, for example, a GaN substrate. The light emitting device 30 is provided on each of the first substrates 10a. The sets of the first substrate 10a and the light emitting device 30 each form a light emitting device chip 31. The light emitting device chips 31 are formed of four light emitting device chips 31. FIG. 10 shows the light emitting device chips 31 in a simplified form for convenience.

The second substrate 10b is provided on the third substrate 10c. The second substrate 10b is, for example, a Si substrate. The imaging device 20 is formed on the second substrate 10b. The second substrate 10b and the imaging device 20 form an imaging device chip 21. The four light emitting device chips 31 are provided around the imaging device chip 21 in the plan view.

Figure 11:
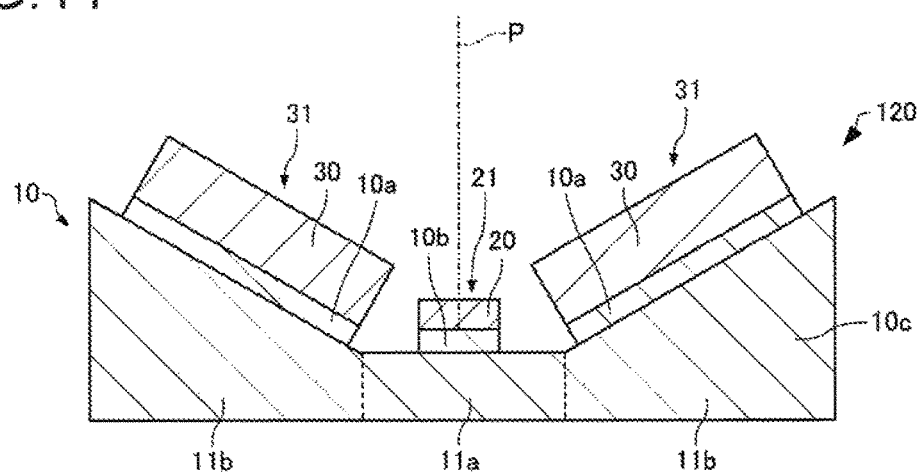
FIG. 11 is a cross-sectional view diagrammatically showing the imaging apparatus according to the second variation of the first embodiment.

The third substrate 10c may include a thin section 11a and a thick section 11b, which is continuous with the thin section 11a and becomes gradually thicker with distance from the thin section 11a, as shown in FIG. 11. The imaging device chip 21 is provided on the thin section 11a. The plurality of light emitting device chips 31 are provided on the thick section 11b. The plurality of light emitting device chips 31 are so arranged that the light beams emitted from the plurality of light emitting device chips 31 intersect one another. The second substrate 10b is, for example, so provided that a normal P to the second substrate 10b passes through the point where the light beams emitted from the plurality of light emitting device chips 31 intersect one another.

In the thus configured imaging apparatus 120, a target to be imaged can be more brightly illuminated by causing the position where the light beams emitted from the plurality of light emitting device chips 31 intersect one another to coincide with the position of the target to be imaged. Further, the thus configured imaging apparatus 120, in which the light emitting device chips 31 can be so arranged relative to the imaging device chip 21 as to be closer to the target to be imaged, can more reliably avoid an undesirable situation in which the imaging device chip is directly irradiated with the light beams emitted from the light emitting device chips 31 and a shadow of the imaging device chip 21 is projected on the target to be imaged.

2. Second Embodiment

2.1. Imaging Apparatus

Figure 12:
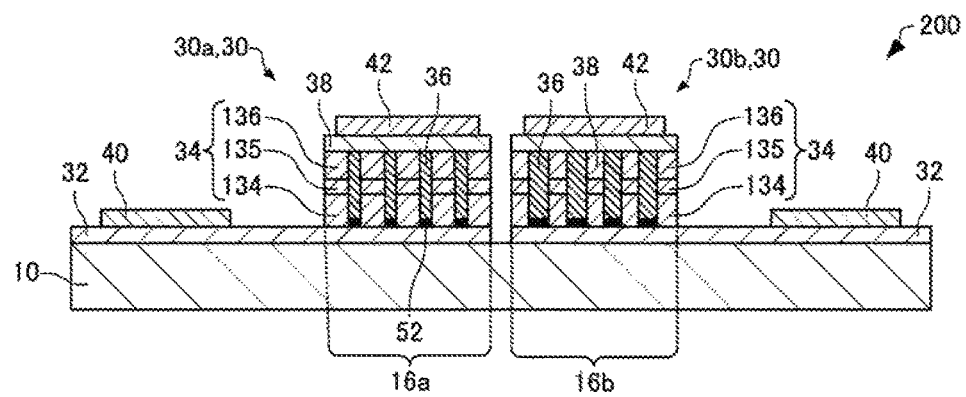
FIG. 12 is a cross-sectional view diagrammatically showing an imaging apparatus according to a second embodiment.
Figure 13:
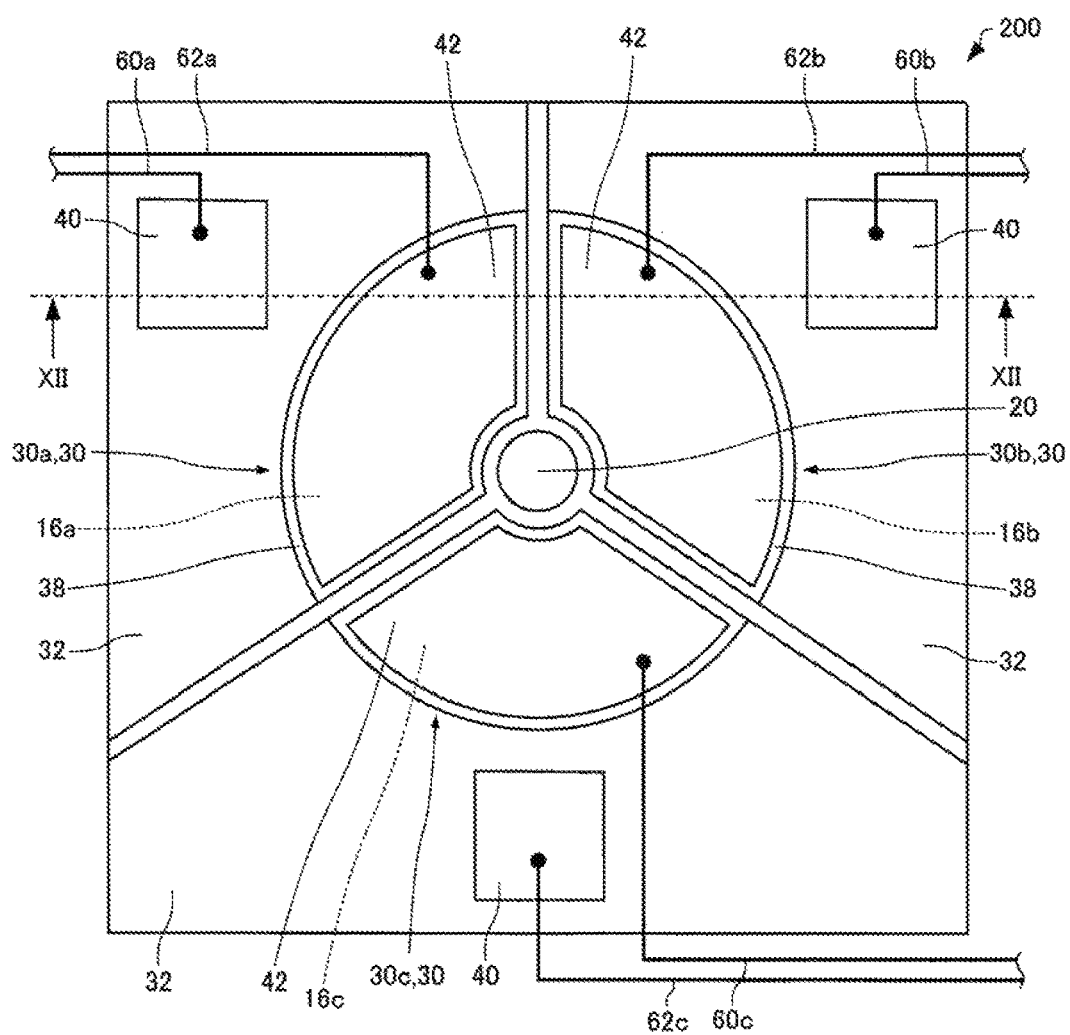
FIG. 13 is a plan view diagrammatically showing the imaging apparatus according to the second embodiment.

An imaging apparatus according to a second embodiment will next be described with reference to the drawings. FIG. 12 is a cross-sectional view diagrammatically showing an imaging apparatus 200 according to the present embodiment. FIG. 13 is a plan view diagrammatically showing the imaging apparatus 200 according to the second embodiment. FIG. 12 is the cross-sectional view taken along the line XII-XII in FIG. 13.

In the imaging apparatus 200 according to the second embodiment in the following description, members having the same functions as those of the constituent members of the imaging apparatus 100 according to the first embodiment described above have the same reference characters and will not be described in detail.

The imaging apparatus 200 differs from the imaging apparatus 100 described above in that the imaging apparatus 200 includes a plurality of light emitting devices 30, as shown in FIGS. 12 and 13, and that the wavelengths of the light beams emitted from the plurality of light emitting devices 30 differ from one another.

In the imaging apparatus 200, the number of light emitting devices 30 is not limited to a specific number. In the example shown in FIGS. 12 and 13, the imaging apparatus 200 includes three light emitting devices 30 (light emitting devices 30a, 30b, and 30c).

The substrate 10 has a first nano-structure formation area 16a, a second nano-structure formation area 16b, and a third nano-structure formation area 16c, in each of which the nano-structures 34 are provided. Specifically, the nano-structures 34 are provided in the nano-structure formation areas 16a, 16b, and 16c via the first contact layer 32. In the example shown in FIG. 13, the first nano-structure formation area 16a is an area that overlaps with the contact layers 32 and 38 of the light emitting device 30a in the plan view. The second nano-structure formation area 16b is an area that overlaps with the contact layers 32 and 38 of the light emitting device 30b in the plan view. The third nano-structure formation area 16c is an area that overlaps with the contact layers 32 and 38 of the light emitting device 30c in the plan view. The nano-structure formation areas 16a, 16b, and 16c are provided, for example, around the imaging device 20 in the plan view.

The diameter of the nano-structures 34 provided in the first nano-structure formation area 16a, the diameter of the nano-structures 34 provided in the second nano-structure formation area 16b, and the diameter of the nano-structures 34 provided in the third nano-structure formation area 16c differ from one another. Therefore, the composition proportion of In in the light emitting layers 135 provided in the first nano-structure formation area 16a, the composition proportion of In in the light emitting layers 135 provided in the second nano-structure formation area 16b, and the composition proportion of In in the light emitting layers 135 provided in the third nano-structure formation area 16c differ from one another. As a result, the wavelength of the light outputted from the nano-structures 34 provided in the first nano-structure formation area 16a, the wavelength of the light outputted from the nano-structures 34 provided in the second nano-structure formation area 16b, and the wavelength of the light outputted from the nano-structures 34 provided in the third nano-structure formation area 16c differ from one another.

For example, the light outputted from the nano-structures 34 provided in the first nano-structure formation area 16a is red light, the light outputted from the nano-structures 34 provided in the second nano-structure formation area 16b is green light, and the light outputted from the nano-structures 34 provided in the third nano-structure formation area 16c is blue light.

In the example shown in FIGS. 12 and 13, the first contact layer 32 of the light emitting device 30a, the first contact layer 32 of the light emitting device 30b, and the first contact layer 32 of the light emitting device 30c are separated from one another. Although not shown, the first contact layers 32 of the light emitting devices 30a, 30b, and 30c may instead be a single continuous layer.

The electrodes 40 and 42 of the light emitting device 30a are connected to wiring lines 60a and 62a, respectively. The electrodes 40 and 42 of the light emitting device 30b are connected to wiring lines 60b and 62b, respectively. The electrodes 40 and 42 of the light emitting device 30c are connected to wiring lines 60c and 62c, respectively. The wiring lines 60a, 62a, 60b, 62b, 60c, and 62c are connected to a drive circuit that is not shown.

The imaging apparatus 200 has, for example, the following features.

In the imaging apparatus 200, the wavelength of the light outputted from the nano-structures 34 provided in the first nano-structure formation area 16a differs from the wavelength of the light outputted from the nano-structures 34 provided in the second nano-structure formation area 16b. Therefore, for example, in a case where the imaging apparatus 200 is used as an endoscope, the wavelength of the light outputted from the imaging apparatus 200 can be selected (switched) in accordance with the type of a diseased site or the application in which the imaging apparatus 200 is used. Since a wavelength that allows a diseased site to be readily observed depends on the type of the diseased side, the imaging apparatus 200 can be used to readily observe the diseased site. In this case, current lower than the threshold current is injected into the light emitting layer 135 of each of the nano-structures 34, and the nano-structure 34 outputs LED light.

In the imaging apparatus 200, for example, the light outputted from the nano-structures 34 provided in the first nano-structure formation area 16a is red light, the light outputted from the nano-structures 34 provided in the second nano-structure formation area 16b is green light, and the light outputted from the nano-structures 34 provided in the third nano-structure formation area 16c is blue light. The imaging apparatus 200 can therefore output light beams having a larger number of wavelengths. For example, the imaging apparatus 200 can output white light. Therefore, in the case where the imaging apparatus 200 is used as an endoscope, a larger number of types of diseased site can be readily observed.

Current higher than or equal to the threshold current may instead be injected into the light emitting layer 135 of each of the nano-structures 34, and the nano-structure 34 may therefore output laser light. In this case, the wavelength of the light outputted from each of the nano-structures 34 may be set in accordance with the application of the endoscope including the imaging apparatus 200. For example, the wavelength of the light outputted from the nano-structures 34 provided in the first nano-structure formation area 16a may be set at a wavelength suitable for incision and excision of a diseased site (405 µm, 10.6 µm, for example), the wavelength of the light outputted from the nano-structures 34 provided in the second nano-structure formation area 16b may be set at a wavelength suitable for blood coagulation and tissue coagulation (488 nm, 515 nm, 1 µm, for example), and the wavelength of the light outputted from the nano-structures 34 provided in the third nano-structure formation area 16c may be set at a wavelength suitable for disinfection (longer than or equal to 350 nm but shorter than or equal to 1 µm, for example). A user may then select the wavelength of the light outputted from the imaging apparatus 200 according to the application. The laser light outputted from each of the light emitting devices 30 including the nano-structures 34 has a narrow radiation angle and is therefore suitable for incision and excision of a diseased site.

2.2. Method for Manufacturing Imaging Apparatus

A method for manufacturing the imaging apparatus 200 according to the second embodiment will next be described. The method for manufacturing the imaging apparatus 200 according to the second embodiment is basically the same as the method for manufacturing the imaging apparatus 100 according to the first embodiment described above and will not therefore be described in detail.

2.3. Variation of Imaging Apparatus

Figure 14:
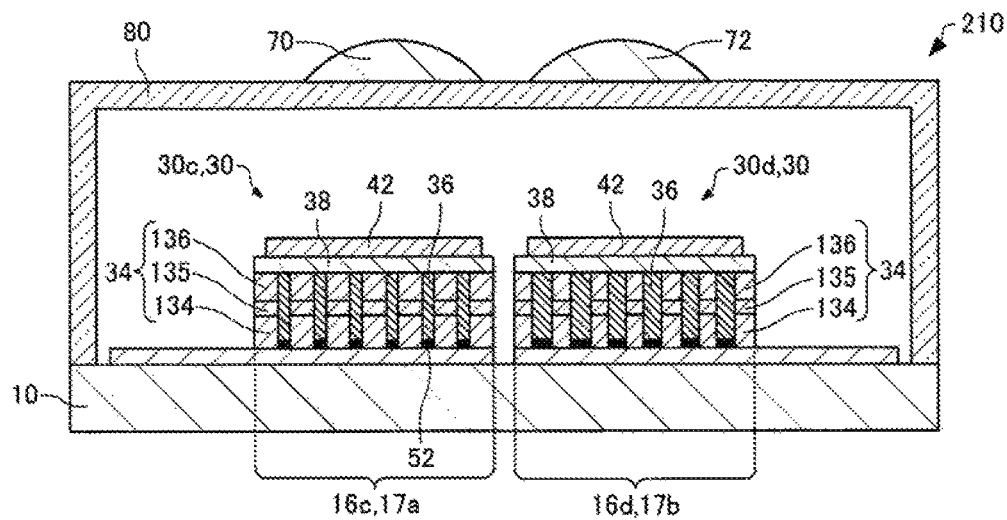
FIG. 14 is a cross-sectional view diagrammatically showing an imaging apparatus according to a variation of the second embodiment.
Figure 15:
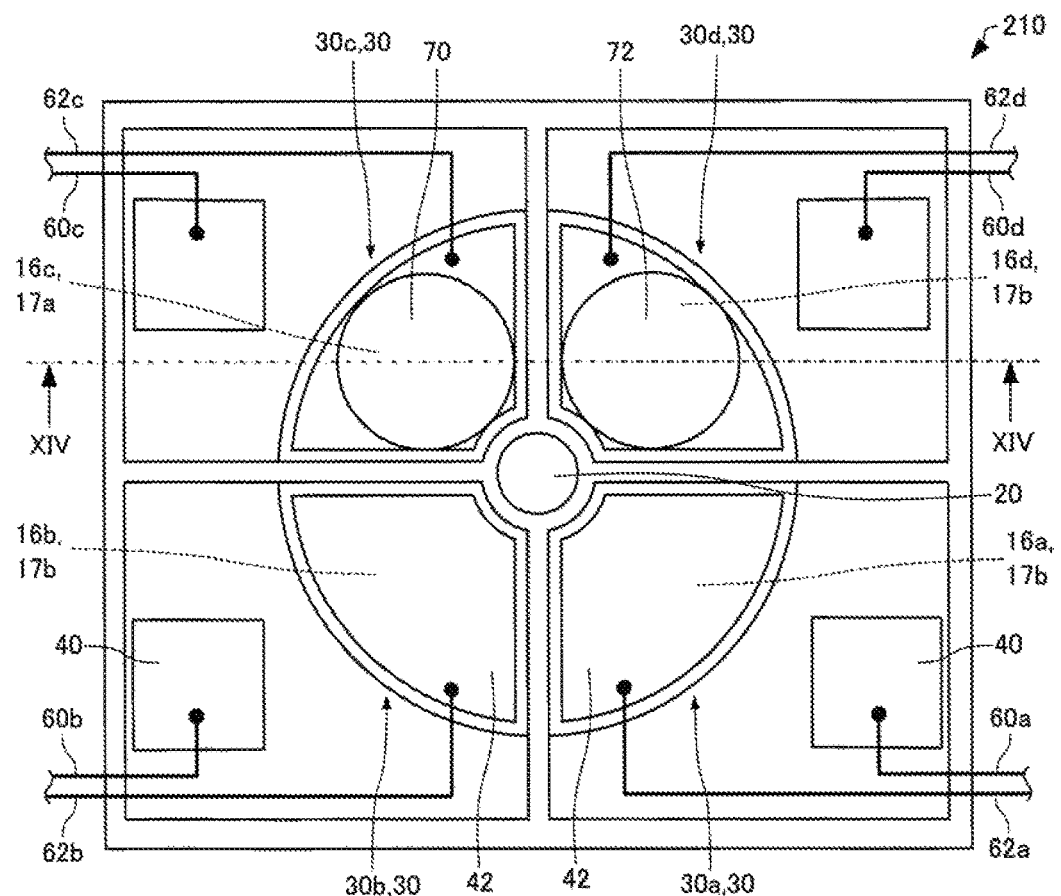
FIG. 15 is a plan view diagrammatically showing the imaging apparatus according to the variation of the second embodiment.

An imaging apparatus according to a variation of the second embodiment will next be described with reference to the drawings. FIG. 14 is a cross-sectional view diagrammatically showing an imaging apparatus 210 according to the variation of the second embodiment. FIG. 15 is a plan view diagrammatically showing the imaging apparatus 210 according to the variation of the second embodiment. FIG. 14 is the cross-sectional view taken along the line XIV-XIV in FIG. 15.

In the imaging apparatus 210 according to the variation of the second embodiment in the following description, members having the same functions as those of the constituent members of the imaging apparatus 100 according to the first embodiment and the imaging apparatus 200 according to the second embodiment described above have the same reference characters and will not be described in detail.

The imaging apparatus 210 differs from the imaging apparatus 200 described above in that the imaging apparatus 210 includes a collector lens 70 and a diffuser lens 72, as shown in FIGS. 14 and 15.

The imaging apparatus 210 includes, for example, four emitting devices 30 (light emitting devices 30a, 30b, 30c, and 30d). The substrate 10 includes a first nano-structure formation area 16a, a second nano-structure formation area 16b, a third nano-structure formation area 16c, and a fourth nano-structure formation area 16d, in each of which the nano-structures 34 are provided. Specifically, the nano-structures 34 are provided in the nano-structure formation areas 16a, 16b, 16c and 16d via the first contact layer 32.

The light emitting device 30a emits, for example, red light. The nano-structures 34 of the light emitting device 30a are provided in the first nano-structure formation area 16a. The light emitting device 30b emits, for example, green light. The nano-structures 34 of the light emitting device 30b are provided in the second nano-structure formation area 16b. The light emitting devices 30c and 30d each emit, for example, blue light. The nano-structures 34 of the light emitting device 30c are provided in the third nano-structure formation area 16c. The nano-structures 34 of the light emitting device 30d are provided in the fourth nano-structure formation area 16d. The electrodes 40 and 42 of the light emitting device 30d are connected to wiring lines 60d and 62d, respectively. The wiring lines 60d and 62d are connected to the drive circuit that is not shown.

The substrate 10 has a laser light outputting area 17a and an LED light outputting area 17b, in each of which the nano-structured 34 are provided, via the first contact layer 32. In the example shown in FIGS. 14 and 15, the third nano-structure formation area 16c is the laser light outputting area 17a, and the fourth nano-structure formation area 16d is the LED light outputting area 17b. Current higher than or equal to the threshold current is injected from the drive circuit that is not shown into the light emitting layers 135 of the nano-structures 34 provided in the laser light outputting area 17a. The light outputted from the nano-structures 34 provided in the laser light outputting area 17a is therefore laser light. In the example shown in FIGS. 14 and 15, the light emitting device 30c includes the nano-structures 34 provided in the laser light outputting area 17a.

Current lower than the threshold current is injected from the drive circuit that is not shown into the light emitting layers 135 of the nano-structures 34 provided in the LED light outputting area 17b. The light outputted from the nano-structures 34 provided in the LED light outputting area 17b is therefore LED light. In the example shown in FIGS. 14 and 15, the light emitting device 30d includes the nano-structures 34 provided in the LED light outputting area 17b.

In the example shown in FIG. 15, the first nano-structure formation area 16a and the second nano-structure formation area 16b are each the LED light outputting area 17b. The light emitting devices 30a and 30b therefore emit LED light. The nano-structure formation areas 16a and 16b may each instead be the laser light outputting area 17a, and in this case, the light emitting devices 30a and 30b each emit laser light.

The imaging apparatus 210 includes, for example, an enclosure 80. The enclosure 80 accommodates the imaging device 20 and the light emitting devices 30. The enclosure 80 is made of a material that can transmit the light emitted from the light emitting devices 30a, 30b, 30c, and 30d. In FIG. 15, the enclosure 80 is not shown for convenience.

The collector lens 70 is located on the outer side of the enclosure 80 and supported by the enclosure 80. The collector lens 70 is so provided as to overlap with the nano-structures 34 of the light emitting device 30c in the plan view. The light emitted from the light emitting device 30c (light outputted from nano-structures 34 provided in laser light outputting area 17a) is incident on the collector lens 70. The collector lens 70 collects the light incident thereon.

The diffuser lens 72 is located on the outer side of the enclosure 80 and supported by the enclosure 80. The diffuser lens 72 is so provided as to overlap with the nano-structures 34 of the light emitting device 30d in the plan view. The light emitted from the light emitting device 30d (light outputted from nano-structures 34 provided in LED light outputting area 17b) is incident on the diffuser lens 72. The diffuser lens 72 diffuses the light incident thereon. The collector lens 70 and the diffuser lens 72 are made, for example, of glass.

Although not shown, the diffuser lens 72 may be provided in a position where the diffuser lens 72 overlaps with the light emitting devices 30a and 30b in the plan view. In a case where the first nano-structure formation area 16a and the second nano-structure formation area 16b are each the laser light outputting area 17a, the collector lens 70 may be provided in a position where the collector lens 70 overlaps with the light emitting devices 30a and 30b in the plan view.

The imaging apparatus 210 has, for example, the following features.

In the imaging apparatus 210, the light outputted from the nano-structures 34 provided in the laser light outputting area 17a is laser light and incident on the collector lens 70, and the light outputted from the nano-structures 34 provided in the LED light outputting area 17b is LED light and incident on the diffuser lens 72. Therefore, in the imaging apparatus 210, the collector lens 70 can output the laser light incident thereon at a narrower angle of radiation, whereby in a case where the imaging apparatus 210 is used as an endoscope, incision and excision can be readily performed on a diseased site. Further, in the imaging apparatus 210, the diffuser lens 72 can output the LED light incident thereon at a wider angle of radiation, whereby in the case where the imaging apparatus 210 is used as an endoscope, a diseased site can be observed over a wider range. For example, in the imaging apparatus 210, the laser light emitted from the light emitting device 30c and the LED light emitted from the light emitting device 30d allow incision or excision of a diseased site and irradiation to the diseased site to be simultaneously performed.

For example, in a case where blood coagulation is performed with laser light, the imaging apparatus according to the second embodiment of the invention may be configured to cause the laser light to be incident on the diffuser lens 72. The blood coagulation can therefore be performed over a wide range.

3. Third Embodiment

Figure 16:
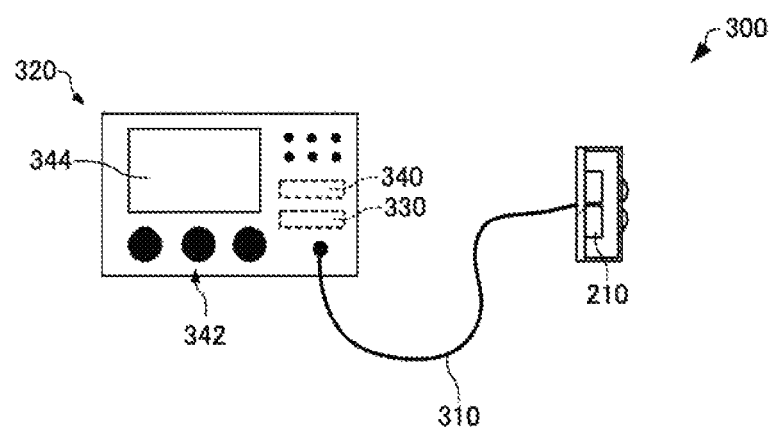
FIG. 16 diagrammatically shows an endoscope according to a third embodiment.

An endoscope according to a third embodiment will next be described with reference to the drawings. FIG. 16 diagrammatically shows an endoscope 300 according to the present embodiment. The endoscope 300 includes the imaging apparatus according to any of the embodiments and variations. The endoscope 300 will be described below on the assumption that it includes the imaging apparatus 210 as one of the imaging apparatus according to the embodiments and variations.

The endoscope 300 includes the imaging apparatus 210, an electric transmission tube 310, and a controller 320, as shown in FIG. 16. The imaging apparatus 210 shown in FIG. 16 is simplified for convenience.

The electric transmission tube 310 connects the imaging apparatus 210 to the controller 320. Specifically, the wiring lines 60a, 60b, 60c, 60d, 62a, 62b, 62c, and 62d are provided in the electric transmission tube 310 with the wiring lines electrically isolated from one another, and the wiring lines are electrically connected to a driver circuit 330 built in the controller 320. A wiring line (not shown) electrically connected to the imaging device 20 is further provided in the electric transmission tube 310. The imaging apparatus 210 and the electric transmission tube 310 are portions inserted into the body of a subject.

The controller 320 includes a processor 340, an operation section 342, and a display section 344.

The operation section 342 is intended to input information necessary for processes carried out by the processor 340. The operation section 342 may, for example, be a button switch, a lever switch, a dial switch, or any of a variety of other switches, a touch panel, a keyboard, or a mouse.

The operation section 342 includes a switch for selecting a light emitting device that is caused to emit light from the light emitting devices 30a, 30b, 30c, and 30d. A user can therefore select the wavelength of the light (color of light) outputted from the imaging apparatus 210.

The operation section 342 further includes a switch for adjusting the amount of current to the light emitting layers 135 of each of the light emitting devices 30a, 30b, 30c, and 30d. The user can therefore select whether the light outputted from the imaging apparatus 210 is the laser light or the LED light. When the user selects, for example, the laser light, the endoscope 300 allows treatment of a diseased site, whereas when the user selects the LED light, the endoscope 300 allows observation of the diseased site. The user can further adjust the intensity of the light outputted from the imaging apparatus 210.

The display section 344 displays an image captured by the imaging apparatus 210. Specifically, the display section 344 can display an image of the diseased site captured by the imaging apparatus 210. The display section 344 is, for example, a LCD (liquid crystal display) or an EL display (electroluminescence display). A single touch-panel-type display may be used to achieve the functions of the operation section 342 and the display section 344.

The processor 340 controls the drive circuit 330. The processor 340 may be achieved by a dedicated circuit and may be configured to carry out the process that will be described later. The processor 340 may further be configured to function, for example, as a computer when a CPU (central processing unit) executes a control program stored in a storage, such as a ROM (read only memory) and a RAM (random access memory) and carry out the process that will be described later. In this case, the storage may have a work area that temporarily stores intermediate data, control results, and other pieces of information resulting from the process.

The processor 340 produces a control signal based on an input signal from the operation section 342 and carries out the process of transmitting the control signal to the drive circuit 330. The drive circuit 330 injects current into the light emitting layers 135 of each of the light emitting devices 30 based on the control signal.

For example, when the user inputs information for causing the light emitting device 30c to emit light and information for causing the light emitting device 30c to output the laser light, the light emitting device 30c emits the laser light to allow treatment based on the laser light. For example, when the user inputs information for causing the light emitting device 30d to emit light and information for causing the light emitting device 30d to output the LED light, the light emitting device 30d emits the LED light to allow treatment based on the LED light. The light emitting devices 30c and 30d may be caused to emit light simultaneously to allow the treatment based on the laser light and the observation based on the LED light to be performed simultaneously.

The endoscope 300 includes the imaging apparatus 210, which allows size reduction. The endoscope 300 therefore allows reduction in size of a portion inserted into the body of a subject.

Although not shown, the endoscope according to the embodiment of the invention may be a capsule-shaped endoscope. In this case, the endoscope according to the embodiment of the invention may be configured to be externally and wirelessly operable. Further, in this case, the endoscope according to the embodiment of the invention may be configured to be fixable in the body. The imaging apparatus according to the embodiment of the invention, which is compact and consumes low electric power because the threshold current value is low, can also be preferably used with the capsule-shaped endoscope.

In the invention, part of the configuration thereof may be omitted or the embodiments and variations may be combined with one another to the extent that the features and effects described in the present application are ensured.

The invention encompasses substantially the same configuration as the configuration described in any of the embodiments (for example, a configuration having the same function, using the same method, and providing the same result or a configuration having the same purpose and providing the same effect). Further, the invention encompasses a configuration in which an inessential portion of the configuration described in any of the embodiments is replaced. Moreover, the invention encompasses a configuration that provides the same advantageous effect as that provided by the configuration described in any of the embodiments or a configuration that can achieve the same purpose as that achieved by the configuration described in any of the embodiments. Further, the invention encompasses a configuration in which a known technology is added to the configuration described in any of the embodiments.

The entire disclosure of Japanese Patent Application No. 2017-097932, filed May 17, 2017 is expressly incorporated by reference herein.

What is claimed is:

1. An imaging apparatus comprising:
a substrate;
an imaging device provided on the substrate; and
a light emitting device provided on a first surface of the substrate and having a plurality of nano-structures,
wherein the light emitting device is configured to emit light,
each of the plurality of nano-structures has a light emitting layer, and
the plurality of nano-structures are arranged along an extending direction of the substrate such that the arrangement of the plurality of nano-structures is configured to cause the light in the light emitting layers to resonate.

2. The imaging apparatus according to claim 1,
wherein the first surface has a nano-structure formation area in which the plurality of nano-structures are provided, and
the nano-structure formation area surrounds the imaging device in a plan view of the first surface.

3. An endoscope comprising the imaging apparatus according to claim 2.

4. The imaging apparatus according to claim 1,
wherein the substrate has a first nano-structure formation area and a second nano-structure formation area in each of which the plurality of nano-structures are provided, and
a wavelength of the light outputted from the plurality of nano-structures provided in the first nano-structure formation area differs from a wavelength of the light outputted from the plurality of nano-structures provided in the second nano-structure formation area.

5. The imaging apparatus according to claim 4,
wherein the substrate has a third nano-structure formation area in which the plurality of nano-structures are provided, the light outputted from the plurality of nano-structures provided in the first nano-structure formation area is red light, the light outputted from the plurality of nano-structures provided in the second nano-structure formation area is green light, and the light outputted from the plurality of nano-structures provided in the third nano-structure formation area is blue light.

6. An endoscope comprising the imaging apparatus according to claim 5.

7. An endoscope comprising the imaging apparatus according to claim 4.

8. The imaging apparatus according to claim 1, further comprising a collector lens and a diffuser lens, wherein the substrate has a laser light outputting area and a LED light outputting area in each of which the plurality of nano-structures are provided, the light outputted from the plurality of nano-structures provided in the laser light outputting area is laser light and is incident on the collector lens, and the light outputted from the plurality of nano-structures provided in the LED light outputting area is LED light and is incident on the diffuser lens.

9. An endoscope comprising the imaging apparatus according to claim 8.

10. The imaging apparatus according to claim 1, wherein the imaging device and the light emitting device are provided on the first surface of the substrate.

11. An endoscope comprising the imaging apparatus according to claim 10.

12. The imaging apparatus according to claim 1, wherein the substrate has a second surface outwardly opposite to the first surface, and the imaging device is provided on the second surface of the substrate.

13. An endoscope comprising the imaging apparatus according to claim 12.

14. An endoscope comprising the imaging apparatus according to claim 1.

15. The imaging apparatus according to claim 1, wherein the substrate has a laser light outputting area and a LED light outputting area in each of which the plurality of nano-structures are provided, and the imaging device is located between the laser light outputting area and the LED light outputting area in a plan view of the first surface.

16. The imaging apparatus according to claim 1, wherein the substrate has a laser light outputting area and a plurality of LED light outputting areas in each of which the plurality of nano-structures are provided, and a number of the laser light outputting area is less than a number of the plurality of LED light outputting areas.

17. An imaging apparatus comprising:

a substrate having a first surface and a second surface outwardly opposite to each other;

an imaging device provided on the first surface of the substrate;

a first contact layer disposed on the first surface of the substrate, the first contact layer having conductivity; and a light emitting device provided on the first contact layer and having a plurality of nano-structures, each of the plurality of nano-structures having a column-shaped cross section when viewed along an extending direction of the substrate, the column-shaped cross section being configured with:
  a first semiconductor layer disposed on the first contact layer;
  a light emitting layer disposed on the first semiconductor layer;
  a second semiconductor layer disposed on the light emitting layer;
  a second contact layer disposed on the second semiconductor layer, the second contact layer having conductivity; and
  a light propagating member configured to propagate emitting light from the light emitting layer, the light propagating member being filled in a gap between two adjacent nano-structures of the plurality of nano-structures, wherein the light emitting layer is sandwiched between the first semiconductor layer and the second semiconductor layer.

18. An imaging apparatus comprising:

a substrate;

an imaging device provided on the substrate; and a light emitting device provided on a first surface of the substrate and having a plurality of nano-structures, wherein each of the plurality of nano-structures is columnar-shaped, and a diameter of one of the plurality of nano-structures is in a range of 50 nm to 500 nm.

* * * * *